(12) United States Patent
Allier et al.

(10) Patent No.: US 11,092,530 B2
(45) Date of Patent: Aug. 17, 2021

(54) OPTICAL METHOD FOR TRACKING THE IN-VITRO AMPLIFICATION OF A NUCLEOTIDE SEQUENCE

(71) Applicant: COMMISSARIAT A L'ENERGIE ATOMIQUE ET AUX ENERGIES ALTERNATIVES, Paris (FR)

(72) Inventors: Cedric Allier, Grenoble (FR); Melissa Baque, Grenoble (FR); Thomas Bordy, Grenoble (FR); Anne-Gaelle Bourdat, Nantoin (FR); Daniel Vellou, Seyssinet (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 428 days.

(21) Appl. No.: 15/897,895

(22) Filed: Feb. 15, 2018

(65) Prior Publication Data
US 2018/0238788 A1 Aug. 23, 2018

(30) Foreign Application Priority Data

Feb. 17, 2017 (FR) ...................................... 1751291

(51) Int. Cl.
| *G01N 15/02* | (2006.01) |
| *G01N 15/14* | (2006.01) |
| *G01N 33/53* | (2006.01) |
| *G01N 21/27* | (2006.01) |
| *G01N 21/47* | (2006.01) |
| *G01N 21/75* | (2006.01) |
| *C12Q 1/6851* | (2018.01) |
| *G01N 21/82* | (2006.01) |
| *C12Q 1/6825* | (2018.01) |
| *G01N 15/00* | (2006.01) |

(52) U.S. Cl.
CPC ....... *G01N 15/0205* (2013.01); *C12Q 1/6825* (2013.01); *C12Q 1/6851* (2013.01); *G01N 15/1468* (2013.01); *G01N 21/272* (2013.01); *G01N 21/4788* (2013.01); *G01N 21/75* (2013.01); *G01N 21/82* (2013.01); *G01N 33/5304* (2013.01); *G01N 2015/0057* (2013.01); *G01N 2015/0065* (2013.01); *G01N 2015/0092* (2013.01); *G01N 2015/0222* (2013.01); *G01N 2015/145* (2013.01); *G01N 2021/755* (2013.01)

(58) Field of Classification Search
CPC .......... G01N 15/0205; G01N 15/1468; G01N 33/5304; G01N 2015/0092; C12Q 1/6825; C12Q 1/6851; C12Q 2525/301; C12Q 2565/301; C12Q 2565/607
See application file for complete search history.

(56) References Cited

U.S. PATENT DOCUMENTS

2016/0291015 A1 10/2016 Huet et al.
2018/0321137 A1* 11/2018 Ismagilov .......... G06K 9/00134

FOREIGN PATENT DOCUMENTS

| EP | 3 115 770 A1 | 1/2017 |
| WO | 2016/151248 A1 | 9/2016 |
| WO | 2016/189257 A1 | 12/2016 |

OTHER PUBLICATIONS

"Imaging Electronics 101: Understanding Camera Sensors for Machine Vision Applications", Edmund Optics, Retrieved from the internet: http://www.edmundoptics.com/resources/applicaton-notes/imaging/understanding-camera-sensors-for-machine-vision-applications/, XP55609583A, 8 pages.
Wang et al.—"Real-time DNA Amplification and Detection System Based on a CMOS Image Sensor", Analytical Sciences Jun. 2016, vol. 32, pp. 653-658.
Arunrut et al.—"Demonstration of a Very Inexpensive, Turbidimetric, Real-Time, RT-LAMP Detection Platform Using Shrimp Laem-Singh Virus (LSNV) as a Model", PLOS ONE, Sep. 2014, vol. 9, Issue 9, pp. 1-11.
Mori et al.—"Real-time turbidimetry of LAMP reaction for quantifying template DNA", J. Biochem. Biophys. Methods 59 (2004), pp. 145-157.
Mori et al.—"Detection of Loop-Mediated Isothermal Amplification Reaction by Turbidity Derived from Magnesium Pyrophosphate Formation", Biochemical and Biophysical Research Communications, (2001), vol. 289, No. 1, pp. 150-154.
Fischbach et al.—"Shining a light on LAMP assays—A comparison of LAMP visualization methods including the novel use of berberine", BioTechniques, Apr. 1, 2015, pp. 189-194.
Preliminary Search Report dated Oct. 23, 2017 issued in corresponding patent FR1751291.
"Imaging Electronics 101: Understanding Camera Sensors for Machine Vision Applications", Edmund Optics, Retrieved from the internet: http://www.edmundoptics.com/resources/applicaton-notes/imaging/understanding-camera-sensors-for-machine-vision-applications/, XP55609583A, 8 pages, Feb. 20, 2016.

* cited by examiner

Primary Examiner — David C Thomas
(74) Attorney, Agent, or Firm — Oblon, McClelland, Maier & Neustadt, L.L.P.

(57) ABSTRACT

The invention relates to a method for tracking the amplification of a sequence of nucleotides in a sample (10). The sample is placed between a light source (12) and an image sensor (16). Under the effect of amplification reagents, mixed with the sample, a nucleotide sequence, called the target sequence, is replicated iteratively, amplifying the target sequence. The method includes the acquisition of an image representative of the formation of a precipitate in the sample under the effect of the amplification, on the basis of which an image of interest is formed. The application of a statistical indicator to the image of interest allows an indicator of the amplification of the target sequence to be determined.

13 Claims, 7 Drawing Sheets

Specification includes a Sequence Listing.

SEQUENCE LISTING

<160> NUMBER OF SEQ ID NOS: 6

<210> SEQ ID NO 1
<211> LENGTH: 18
<212> TYPE: DNA
<213> ORGANISM: Escherichia coli -continued

```
<400> SEQUENCE: 1
gccatctcct gatgacgc                                                    18

<210> SEQ ID NO 2
<211> LENGTH: 18
<212> TYPE: DNA
<213> ORGANISM: Escherichia coli

<400> SEQUENCE: 2
atttaccgca gccagacg                                                    18

<210> SEQ ID NO 3
<211> LENGTH: 40
<212> TYPE: DNA
<213> ORGANISM: Escherichia coli

<400> SEQUENCE: 3
ctggggcgag gtcgtggtat tccgacaaac accacgaatt                            40

<210> SEQ ID NO 4
<211> LENGTH: 42
<212> TYPE: DNA
<213> ORGANISM: Escherichia coli

<400> SEQUENCE: 4
cattttgcag ctgtacgctc gcagcccatc atgaatgttg ct                         42

<210> SEQ ID NO 5
<211> LENGTH: 24
<212> TYPE: DNA
<213> ORGANISM: Escherichia coli

<400> SEQUENCE: 5
ctttgtaaca acctgtcatc gaca                                             24

<210> SEQ ID NO 6
<211> LENGTH: 25
<212> TYPE: DNA
<213> ORGANISM: Escherichia coli

<400> SEQUENCE: 6
atcaatctcg atatccatga aggtg                                            25
```

OPTICAL METHOD FOR TRACKING THE IN-VITRO AMPLIFICATION OF A NUCLEOTIDE SEQUENCE

TECHNICAL FIELD

The technical field of the invention is that of methods for tracking the amplification of a nucleotide sequence.

PRIOR ART

Selective amplification of a nucleotide sequence, such a fragment of DNA or RNA, has advanced considerably since the development of the polymerase-chain-reaction method, usually referred to by the acronym PCR for "polymerase chain reaction". Such a method allows copies of a sequence of nucleotides initially present in a sample to be obtained by implementing methods that are now well standardized. The applications are numerous, in particular in the field of cloning of specific DNA fragments, in the detection and identification of genes for the diagnosis of genetic disorders, or in legal medicine. Among applications outside of the health field, mention may be made of the inspection of foodstuffs, and, for example, of the detection of the presence of genetically modified DNA. One of the drawbacks of PCR is however the need to carry out precise thermal cycles.

Recently, alternative amplification methods to PCR have appeared that are able to work under isothermal conditions and that do not require thermal cycles to be repeated. For example, the method referred to by the acronym LAMP, for "Loop-mediated isothermal amplification of DNA", which was discovered near the turn of the century and is described in the publication Notomi T, "Loop-mediated isothermal amplification of DNA", Nucleic Acids Research, 2000, Vol. 28, No. 12, is noteworthy. This method has many advantages. In particular it may be implemented at constant temperature and has a high specificity and a high amplification efficiency. The publication: Hill Joshua "Loop-Mediated Isothermal Amplification Assay for Rapid Detection of Common Strains of *Escherichia coli*", Journal of Clinical Microbiology, August 2008, page 2800-2804, describes the use of LAMP amplification to detect strains of *Escherichia coli*. This publication is referred to as "Hill 2008" below.

Whatever the amplification method employed, it is often necessary to monitor the progress of the amplification reaction. To do this, optical methods have been developed, in particular methods involving adding a fluorescent label to the sample, allowing amplification to be correlated to a detected level of fluorescence. In addition or alternatively to the fluorescent label, a dye may also be used, so as to allow amplification to be tracked optically.

However, the addition of exogenous dyes or fluorescent agents may have consequences on the amplification process and/or may be associated with a toxicity risk. In addition, this has an impact on the cost and complexity of the operation. Specifically, detection of a fluorescent signal requires sensitive sensors equipped with an optical filter centered on the wavelength of fluorescence. The dyed or fluorescent reagents also themselves have a non-negligible additional cost, and their use increases the complexity of the method.

The publication Mori Y. "Real-time turbidimetry of LAMP reaction for quantifying template DNA", J. Biochem. Biophys. Methods 59 (2004) 145-157, describes an optical method for tracking in-vitro amplification of a DNA sequence via measurement of a turbidity of the sample. In this publication, a nucleic acid is amplified by LAMP. The sample is placed between a light source and a photodiode. On the basis of the intensity of the signal measured by the photodiode, a quantity representative of a turbidity of the medium, which is amplification-dependent, is determined. The sample is placed in tubes of 2.5 mm diameter, the light source and the photodiode being radially opposite. The publication Mori Y. "Detection of Loop-Mediated Isothermal Amplification Reaction by Turbidity Derived from Magnesium Pyrophosphate Formation", Biochemical and Biophysical Research Communications 289, 150-154 (2001), attributes the change in the turbidity to the formation of magnesium pyrophosphate during the LAMP amplification. Such a method is now implemented industrially, for example in the Loopamp® device sold by Eiken.

However, this method is not suitable for reaction media that are too opaque, for example media containing blood. Specifically, the absorption is too high and the measured signal is more dominated by optical attenuation than by the scattering resulting from the change in the turbidity of the medium. In addition, the sensitivity of this method is limited as a relatively large amount of magnesium pyrophosphate must be formed before a significant attenuation of the light emitted by the source is obtained.

The inventors have developed an optical method for tracking a reaction for amplifying a sequence of nucleotides without marker addition, having a higher sensitivity than the prior art. In addition, the method is suitable for colored reaction media. Its application is simple and inexpensive. Furthermore, the method may be implemented in compact and portable devices. Moreover, the method is compatible with most currently available methods for amplifying nucleotide sequences.

SUMMARY OF THE INVENTION

A first subject of the invention is a method for tracking an in-vitro amplification of a nucleotide sequence contained in a sample, the amplification aiming to replicate said nucleotide sequence via a polymerase DNA enzyme, the method comprising the following steps:
  a) mixing the sample with amplification reagents so as to obtain multiple replications of a preset nucleotide target sequence, the mixing being carried out at an initial time;
  b) illuminating the sample using a, preferably spatially coherent, light source, the light source emitting, in an illumination spectral band, an incident light wave that propagates toward the sample;
  c) acquiring, using an image sensor, a two-dimensional image of the sample, in the illumination spectral band, the sample being placed between the light source and the image sensor such that the image sensor is exposed to what is called an exposure light wave having passed through the sample, the acquisition being carried out at an acquisition time subsequent to the initial time;
  d) on the basis of the acquired image, forming an image of interest that is representative of the formation of a precipitate in the sample under the effect of the amplification; and
  e) determining an indicator, called the amplification indicator, depending on a distribution of the intensity of the pixels in all or some of the image of interest, the amplification indicator being representative of a replicated amount of target sequences.

The amplification indicator preferably is a dispersion of the intensity of pixels in all or some of the image of interest.

According to one embodiment, in step e), the amplification indicator is determined using a statistical indicator representing a mean, a median or a dispersion of a distribution of the intensity of the pixels composing the image of interest. The amplification indicator may be determined by calculating a moment of order strictly higher than 1 of said distribution. The moment may be a central moment or a standardized moment.

The amplification indicator may allow a time, called the threshold time, at which the amplification indicator crosses a preset threshold, to be determined.

The exposure light wave may in particular be formed from a portion of the incident light wave that is not absorbed by the sample, and from a wave resulting from the diffraction, by the sample, of the incident light wave. The larger the amount of precipitate in the sample, the more the diffraction of the incident light wave by the sample is significant, and observable in the image acquired by the image sensor.

According to one embodiment, the image of interest corresponds to all or some of the acquired image.

According to another embodiment, the image of interest is obtained by applying a holographic reconstruction operator to all or some of the acquired image. In this case, step d) of the method includes the following substeps:
  di) to all or some of the image acquired in step c), applying a propagation operator so as to calculate a complex amplitude of the exposure light wave, on a reconstruction surface lying facing the image sensor, and
  dii) on the basis of the complex amplitude, forming an image, called the reconstructed image, representative of the modulus and/or phase of said complex amplitude on the reconstruction surface, the reconstructed image then forming the image of interest.

The reconstruction surface may be a plane parallel to a plane, called the detection plane, in which the image sensor lies, and that preferably passes through the sample.

The indicator calculated in step e) may be obtained by applying a statistical indicator to the image reconstructed in substep dii). It may in particular be a mean value or median. It may also be a moment of order higher than 1 of the distribution of the intensity of pixels of the reconstructed image, the latter forming the image of interest. Preferably, the statistical indicator is obtained from the variance or standard deviation of the distribution.

Steps b) to c) are preferably implemented during the replication of the target sequence. They are generally implemented iteratively, in order to observe the temporal variation in the amplification indicator, the latter depending on the number of target sequences replicated. Thus, steps a) to e) may be carried out at various acquisition times, the method then including a step f) of tracking the value of the amplification indicator. Specifically, the amplification is accompanied by the formation of pyrophosphate ions in the sample under the effect of the replication of the target sequence. The formation of an insoluble precipitate from the phosphate ions has an influence on the light-scattering and light-diffracting properties of the sample. The presence of such precipitates may be detected in the image formed in step c). The precipitate formed may be magnesium pyrophosphate.

The method may include a step g) of detecting a time, called the threshold time, at which the amplification indicator passes a threshold value, so as to obtain a length of time, or time span, between the threshold time and the initial time.

The amplification may be achieved by polymerase-chain-reaction amplification and in particular isothermal polymerase-chain-reaction amplification.

The sample is preferably contained in a fluidic chamber the thickness of which is smaller than 1 mm, the area of the sample observed by the image sensor being larger than 10 $mm^2$.

Preferably, in step a) the reagents mixed with the sample with a view to obtaining replication of the target sequence are suitable for forming a precipitate from pyrophosphate ions liberated during the replication of the target sequences. After the mixing, there may in particular be no pyrophosphatase in the sample, or an amount of pyrophosphatase that is sufficiently small to allow a sufficiently large amount of a precipitate to form from the pyrophosphate ions. By sufficiently large amount to form, what is meant is a concentration of at least 0.5 mM, or even of at least 1 mM. After the mixing, the sample contains ions allowing an insoluble precipitate to form from the pyrophosphate ions resulting from the amplification process. It may for example be a question of manganese ions or magnesium ions.

By nucleotide sequence, what is for example meant is a segment of a nucleic acid. The amplification in particular consists in the use of primers specific to the target sequence to be amplified, the primers being able to hybridize on either side of the sequence to be amplified, and in the use of a polymerase enzyme. The polymerase enzyme allows a strand of polynucleotides to be synthesized.

The amplification may be obtained by polymerase chain reaction and preferably isothermal polymerase chain reaction.

Preferably, no magnifying or image-forming optics are placed between the sample and holder.

A second subject of the invention is a device for tracking the in-vitro amplification of a sequence of nucleotides in a sample, the device including:
  a point light source able to emit an incident light wave that propagates toward the sample;
  a holder, configured to hold the sample between the light source and an image sensor; and
  a processor configured to receive an image of the sample, which image is acquired by the image sensor, and to implement steps c) to e) of the first subject of the invention.

According to one embodiment, no image-forming or magnifying optics are placed between the image sensor and holder.

A third subject of this patent application is a method for tracking the in-vitro amplification of a nucleotide sequence, contained in a sample, the amplification aiming to replicate said nucleotide sequence via a polymerase DNA enzyme, the method including the following steps:
  i) mixing the sample with what are called amplification reagents that are apt to obtain multiple replications of a preset nucleotide sequence called the target sequence, the mixing being carried out at an initial time;
  ii) illuminating the sample using a light source, the light source emitting an incident light wave that propagates toward the sample;
  iii) acquiring, using a photodetector, what is called an exposure light wave having passed through all or some of the sample, the acquisition being carried out at an acquisition time subsequent to the initial time; and
  iv) determining an indicator of amplification of the target sequence from an indicator, called the amplification indicator, determined depending on an intensity of the exposure light wave detected in step iii);

the method including introducing, into the sample, a reagent suitable for forming pyrophosphate ions in the latter.

The reagent may be a pyrophosphate salt, for example potassium pyrophosphate.

Preferably, the reagent suitable for forming pyrophosphate ions in the sample is introduced prior or simultaneously to the amplification reagents.

When the sample contains magnesium or manganese, it enables early detection of the amplification of the target nucleotide sequence.

The amplification indicator may quantify an absorption of the incident light wave by the sample. In this specific embodiment, the exposure light wave may be a wave emitted in a spectral band different from the spectral band of the illumination wave, a fluorescence for example. According to one embodiment, the exposure light wave is formed from interference between the incident light wave not absorbed by the sample and a wave resulting from the diffraction of the incident light wave by the sample.

According to this embodiment, the photodetector may be a photodiode or an image sensor. According to this embodiment, the method may have the features of the first subject of the invention.

The amount of reagent suitable for forming pyrophosphate ions is such that the concentration of pyrophosphate ions in the sample, before the replication of the target sequences, is preferably comprised between 0.01 mM and 0.5 mM, and preferably between 0.05 mM and 0.5 mM.

Other advantages and features will become more clearly apparent from the following description of particular embodiments of the invention, which are given by way of non-limiting example and illustrated in the figures listed below.

DESCRIPTION OF PARTICULAR EMBODIMENTS

Figure 1:
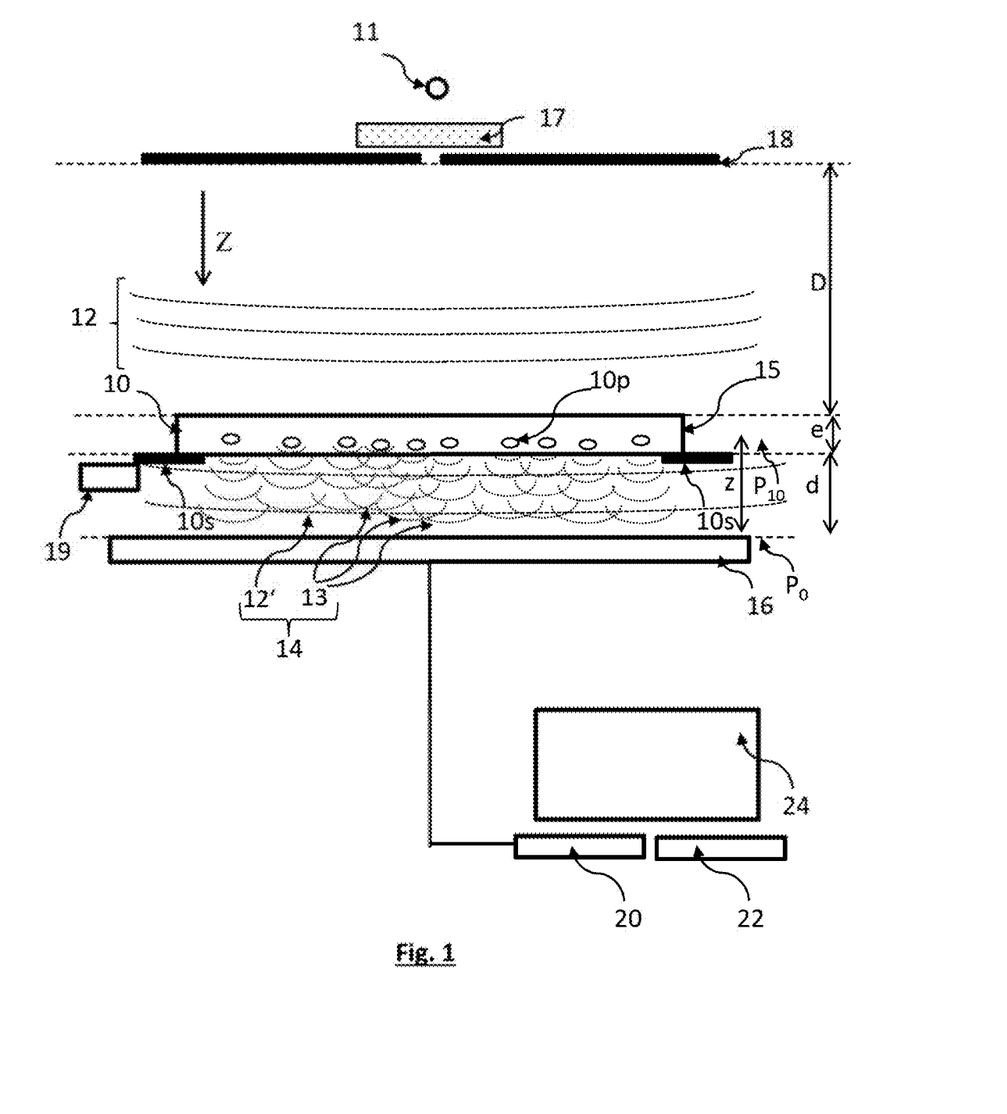
FIG. 1 is an example of a device allowing the invention to be implemented.

FIG. 1 shows an example of a device according to the invention. A light source 11 emits a light wave 12, called the incident light wave, that propagates toward a sample 10, along a propagation axis Z. The light wave is emitted in a spectral band $\Delta\lambda$.

The sample 10 is a sample including a nucleotide sequence, called the target sequence, that it is desired to replicate. This nucleotide sequence may in particular be a fragment of DNA. The sample also contains reagents, forming a reaction medium, allowing DNA fragments to be replicated, this process also being referred to as amplification. The amplification factor, i.e. the number of sequences replicated from a target sequence, may exceed $10^2$ or even $10^6$ or more. The sample is liquid. Amplification reagents are commercially available, in particular in the form of kits.

The sample 10 is, in this example, contained in a fluidic chamber 15. The fluidic chamber 15 is for example a fluidic chamber of thickness e=250 µm. The thickness e of the fluidic chamber 15, along the propagation axis Z, typically varies between 10 µm and 1 cm, and is preferably comprised between 20 µm and 500 µm. The sample 10 lies in a plane $P_{10}$, called the sample plane, preferably perpendicular to the propagation axis Z. It is held on a holder 10s at a distance d from an image sensor 16. The area over which the sample extends, parallelly to the image sensor 16, is preferably larger than 1 mm$^2$ and is preferably larger than 5 mm$^2$ or even 10 mm$^2$. Thus, preferably, the sample is not very thick (less than 1 mm thick) and extends over an area of several mm$^2$. Such a configuration allows the sensitivity of the method to be increased, as described below with regard to the experimental trials. A radiator 19 allows the sample, contained in the fluidic chamber, to be maintained at a set-point temperature, a set-point temperature comprised between 60° C. and 65° C. for example.

The distance D between the light source 11 and the sample 10 is preferably larger than 1 cm. It is preferably comprised between 2 and 30 cm. Advantageously, the light source, seen by the sample, may be considered to be point like. This means that its diameter (or its diagonal) is preferably smaller than one tenth, and better still one hundredth, of the distance between the sample and the light source. The light source 11 may be a light-emitting diode or a laser diode. When the light source is a light-emitting diode, it is preferably associated with a diaphragm 18 i.e. a spatial filter. The aperture of the diaphragm is typically comprised between 5 µm and 1 mm and is preferably comprised between 50 µm and 500 µm. In this example, the diaphragm is the Thorlabs diaphragm of reference P150S, and its diameter is 150 µm. The diaphragm may be replaced by an optical fiber playing the role of spatial filter, one end of which is placed facing the light source 11 and the other end of which is placed facing the sample 10.

The device may include a diffuser 17, placed between the light source 11 and the diaphragm 18. The use of such a diffuser allows constraints on the centrality of the light source 11 with respect to the aperture of the diaphragm 18 to be relaxed. The function of such a diffuser is to scatter the light beam produced by the light source over a cone of angle α. Preferably, the scattering angle α varies between 10° and 80°. The presence of such a diffuser allows the device to be made more tolerant to decentering of the light source with respect to the diaphragm. The diaphragm 18 is not essential, in particular when the light source is sufficiently point-like and especially when it is a laser source.

Preferably, the emission spectral band Δλ of the incident light wave 12 has a width smaller than 100 nm. By spectral bandwidth, what is meant is a full width at half maximum of said spectral band.

The sample 10 is placed between the light source 11 and the aforementioned image sensor 16. The latter preferably lies parallel, or substantially parallel, to the plane $P_{10}$ in which the sample lies. The term substantially parallel means that the two elements may not be rigorously parallel, an angular tolerance of a few degrees, smaller than 20° or 10°, being acceptable.

The image sensor 16 is able to form an image $I_0$ of the sample in a detection plane $P_0$. In the example shown, the image sensor 16 includes a matrix-array of pixels, of CCD or CMOS type. The detection plane $P_0$ is preferably perpendicular to the propagation axis Z of the incident light wave 12. The distance d between the sample 10 and the matrix-array of pixels of the image sensor 16 is preferably comprised between 50 µm and 2 cm and preferably comprised between 100 µm and 2 mm. The detection area of the image sensor is preferably larger than 10 mm².

The absence of magnifying optics between the image sensor 16 and the sample 10 will be noted. This does not prevent focusing microlenses possibly being present level with each pixel of the image sensor 16, these lenses not having the function of magnifying the image acquired by the image sensor. The absence of magnifying optics allows the image sensor to be placed close to the sample, in the distance range described in the preceding paragraph. This increases the compactness of the device.

Prior to the acquisition of an exploitable image, the sample is mixed with amplification reagents, forming a reaction medium, apt to engender an amplification of the target sequence. The reaction medium in particular contains:
  primers, able to hybridize on either side of the target sequence, the typical length of these primers for example being comprised between 10 and 50 nucleotides;
  a polymerase enzyme (many polymerase enzymes are commercially available at the present time);
  deoxynucleotide solutions; and
  a buffer, the composition of which depends on the type and characteristics of the enzyme used. The buffer may in particular include magnesium ions, for example in the form of magnesium chloride. The magnesium ions catalyze the action of the polymerase enzyme. The buffer includes ions allowing an insoluble precipitate to be obtained from the pyrophosphate ions formed by the amplification. The buffer may also include manganese ions.

In the preferred embodiment, the target sequence is amplified by LAMP amplification, such as described with reference to the prior art. The fact that the amplification is isothermal simplifies the process and the design of the device implementing the invention, since the sample is held at a constant temperature, typically between 60° C. and 65° C. It has been observed, in the prior art, that replication of the target sequence liberates pyrophosphate ions $P_2O_7^{4-}$. The latter interact with the $Mg^{2+}$ ions to form a complex $[Mg]^{2+}[P_2O_7]$ (magnesium pyrophosphate) that appears in the form of a magnesium-pyrophosphate precipitate 10p. The formation of precipitates from other ions, $Mn^{2+}$ ions for example, is also possible.

Thus, as the amplification of the target sequence progresses, the concentration of magnesium pyrophosphate increases, thereby increasing the scattering coefficient of the sample; the sample becomes turbid and scatters light more. Moreover, the higher the magnesium pyrophosphate concentration, the more the incident light wave is diffracted by the sample.

The inventors have observed that the formation of an image of the sample allows early observation of the formation of the precipitate 10p formed by the pyrophosphate ions during the amplification process. This allows the amplification to be tracked visually in a large sample area. Rather than detecting, using a photodiode, a variation in the intensity of a light beam passing through a sample thickness of a few millimeters, as in the prior art, the inventors have observed that it is preferable to form an image of a light beam passing through a small thickness of sample, the acquired image being of a large detection area, typically a detection area larger than 5 mm² and preferably larger than 10 mm². In other words, a small-thickness/large-area configuration is preferable to the large-thickness/small-area configuration of the prior art.

Under the effect of the incident light wave 12, the precipitates 10p formed in the sample may engender a diffracted wave 13, liable to interfere, in the detection plane $P_0$, with a portion of the incident light wave that is not absorbed by the sample and that is transmitted by the latter. Moreover, the sample 10 may absorb a portion of the incident light wave 12, in particular when it is colored. Thus, the light wave 14, called the exposure light wave, which is transmitted by the sample and to which the image sensor 16 is exposed, may comprise:
  a component 13 resulting from diffraction of the incident light wave 12 by the sample, and in particular by the precipitates 10p formed in the latter; and
  component 12' including a portion of the incident light wave 12 transmitted by the sample, after partial absorption of the latter by the sample.

These components interfere in the detection plane. Thus, the image acquired by the image sensor contains interference patterns (or diffraction patterns), the latter resulting from the precipitates 10p formed in the sample. The reason these diffraction patterns are obtained is that the incident light wave 12 is produced by a spatially coherent source. It reaches the sample in the form of plane waves. The component 12' resulting from the absorption of the incident light wave 12 reaches the image sensor 16 in the form of plane waves, this being propitious to the obtainment of interference patterns in the detection plane.

A processor 20, for example a microprocessor, is configured to process each image $I_0$ acquired by the image sensor 16. In particular, the processor is a microprocessor connected to a programmable memory 22 in which is stored a sequence of instructions for performing the image-processing and calculating operations described in this description. The processor may be coupled to a screen 24 allowing images acquired by the image sensor 16 or processed by the processor 20 to be displayed.

The use of a fluidic chamber 15 of small thickness, typically smaller than 1 mm, and preferably smaller than 500 µm, or even 100 µm, is particularly appropriate when the samples are colored, for example when the samples contain blood. The small thickness of the chamber allows the absorption of the light passing through the sample to be minimized. Moreover, acquiring an image $I_0$ of a large area, larger than 5 mm² or 10 mm², allows a region of interest ROI, or a plurality of regions of interest, propitious to the determination of an amplification indicator k to be identified. The identification of regions of interest in the acquired image $I_0$ allows the formation of precipitates 10p in the fluidic chamber 15, reflecting an amplification of the target sequence, to be detected early.

According to a first embodiment, on the basis of the image $I_0$ acquired by the image sensor 16, an image I, called the image of interest, is formed. The image of interest I corresponds to the acquired image $I_0$ or to a region of interest ROI selected in the acquired image $I_0$. The inventors have observed that it is preferable to use indicators expressing a dispersion of the intensity of the pixels of the image of interest, rather than indicators based on a mean or median of the intensity of the pixels of the image. Such a dispersion may be quantified by a variance or a standard deviation, or, generally, using a moment of order higher than 1 of a distribution of the intensity of the pixels of the image of interest. The dispersion indicator may be a moment of the distribution, in particular a moment $m_r$ of order r strictly higher than 1 of the distribution. The dispersion indicator may for example be obtained from the skewness (standardized moment of order 3) or from the kurtosis (standardized moment of order 4).

Figure 2A:
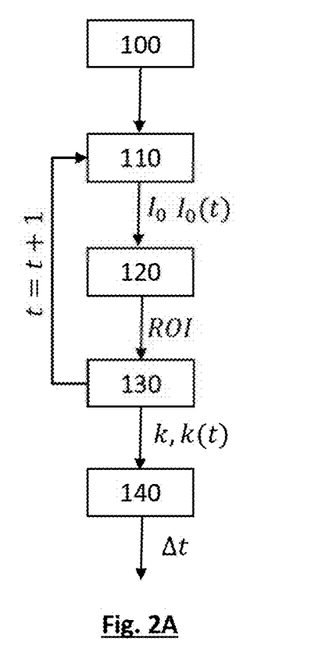
FIG. 2A shows the main steps of one embodiment.

FIG. 2A summarizes the main steps of the method according to this first embodiment.

Step 100: preparation of the sample: in this step, the sample 10, containing an initial amount of target sequences, is mixed with a reaction medium allowing the target nucleotide sequence to be amplified and an insoluble precipitate 10p to be formed, then introduced into the fluidic chamber 15. The time $t_0$ corresponding to the mixing is called an initial time.

Step 110: image acquisition. The sample 10 is illuminated with the light source 11 and an image $I_0$ is acquired with the image sensor 16.

Step 120: selection of a zone of interest. A region of interest ROI is selected in the acquired image. This step is optional, the region of interest possibly being the entire acquired image.

Step 130: determination of an amplification indicator k from the image $I_0$ acquired in step 110 or of the zone of interest ROI selected in step 120. The amplification indicator k is preferably representative of a texture of the image or of a dispersion of the intensity of the pixels of the image. It may in particular be obtained from a moment of the distribution of the pixels and more particularly a moment of order strictly higher than 1.

Steps 110 to 130 may be reiterated so as to obtain, at various times t, acquired images $I_0(t)$ and/or images of interest I(t), an amplification indicator k(t) being determined for each image of interest. This allows a temporal variation in the amplification factor k(t) to be obtained. It is then possible to determine a time, called the threshold time $t_s$, at which the amplification indicator passes a threshold value $k_{th}$. The threshold value $k_{th}$ may be a set value that is determined beforehand, for example in trials on known standard calibration samples. The time span Δt between the threshold time $t_s$ and the initial time $t_0$ depends on the amount of target sequences at the initial time. The longer the time span Δt, the lower the initial amount of target sequences. The threshold time $t_s$ is determined in step 140.

A series of trials has been carried out, using a sample of a solution of purified DNA extracted from an *Escherichia coli* culture and placed in a Countess® fluidic chamber of 250 µm thickness, the examined volume being 8 mm³, i.e. 8 µl. The target nucleotide sequence is the gene *E. coli* mal B.

The reaction medium contained:
  a buffer supplied by NEB under the reference B0537S, containing 20 mM of Tris-HCl buffer, 50 mM KCl, 10 mM $(NH_4)_2SO_4$, 2 mM $MgSO_4$, and 0.1% Tween (registered trademark) 20, the pH being 8.8 at 25° C.;
  1.2 mM of a kit of free deoxyribonucleotide triphosphate (dNTP) solutions, supplied by Sigma-Aldrich under the reference DNTP100A-1KT;
  0.32 U/µl of the DNA polymerase enzyme Bst3 (*Bacillus stearothermophilus*), U being the enzyme unit;
  0.8 M of betaine (Sigma-Aldrich B0300); and
  4 mM $MgSO_4$ (Sigma-Aldrich B1003S), so as to obtain $Mg^{2+}$ ions in the reaction medium.

The primers used are described in the publication [Hill 2008] cited in the prior art, and described in the listing appended to the description. It is a question of:
  GCCATCTCCTGATGACGC) (SEQ ID NO: 1) (outer forward—concentration 0.2 µM;
  ATTTACCGCAGCCAGACG) (SEQ ID NO: 2) (outer backward—concentration 0.2 µM);
  CTGGGGCGAGGTCGTGGTATTCCGACAAACAC-CACGAATT) (SEQ ID NO: 3) (inner forward—concentration 1.6 µM);
  CATTTTGCAGCTGTACGCTCGCAGCCCATCAT-GAATGTTGCT) SEQ ID NO: 4) (inner backward—concentration 1.6 µM);
  CTTTGTAACAACCTGTCATCGACA) (SEQ ID NO: 5) (loop forward—concentration 0.8 µM);
  ATCAATCTCGATATCCATGAAGGTG) (SEQ ID NO: 6) (loop backward—concentration 0.8 µM).

A base solution was elaborated, containing an amount of about $10^6$ copies of the target sequence per microliter. This amount was evaluated using a reference method (the Qubit® method).

The other elements of the experimental set-up were as follows:
  light source 11: Cree MC-E Color light-emitting diode, this diode including three light-emitting diodes respectively emitting in the following spectral bands Δλ: 450 nm-465 nm; 520 nm-535 nm; 620 nm-630 nm. In this example, a single diode, the diode emitting in the 450 nm-465 nm spectral band, was activated for each illumination;
  image sensor 16: monochromic CMOS sensor of 3840×2748 pixels, each pixel having a side length of 1.67 µm, the detection area being about 30 mm², the observed field being 6.4 mm×4.6 mm;
  distance D between the light source 11 and the sample 10: 5 cm;
  distance d between the sample 10 and the image sensor 16: 2 mm;
  thickness e of the fluidic chamber 15: 250 µm;

diameter of the aperture of the spatial filter 18: 150 μm; and temperature of the sample: 65° C.

The sample was mixed with the reaction medium at the initial time t0, then the mixture was introduced into the fluidic chamber 15.

Figure 3A:
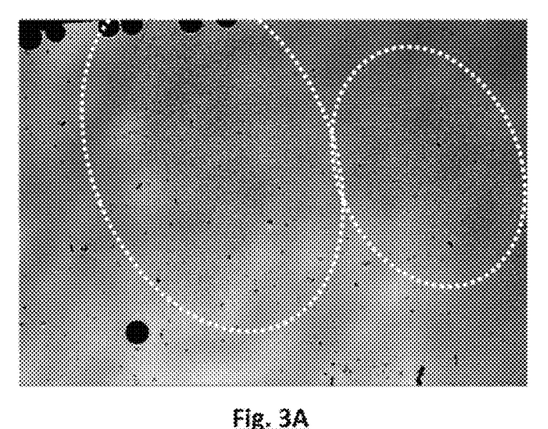
FIG. 3A shows an image of a sample containing between 30 and 35 copies of a target sequence, the image being acquired 40 minutes after the sample and a reaction medium containing amplification reagents were mixed.

FIG. 3A is an image acquired by the image sensor 16 forty minutes after the mixing of a first sample with the reaction medium. The first sample initially included 100 copies of the target sequence in a volume of 25 μl (microliters). The observed volume was estimated to be 8 μl, this corresponding to about 30 to 35 copies. Two regions of interest ROI (each encircled with a circle) were observed to appear. The regions of interest ROI corresponded to regions in which a granularity formed in the image. The texture of the image was attributed to the formation of precipitates 10p of magnesium pyrophosphate in the sample. The image acquisition allowed regions of interest to be identified in which the morphology of the image was observed to vary. It was thus possible to observe the amplification of the target sequence at an earlier stage than in the prior art.

Figure 3B:
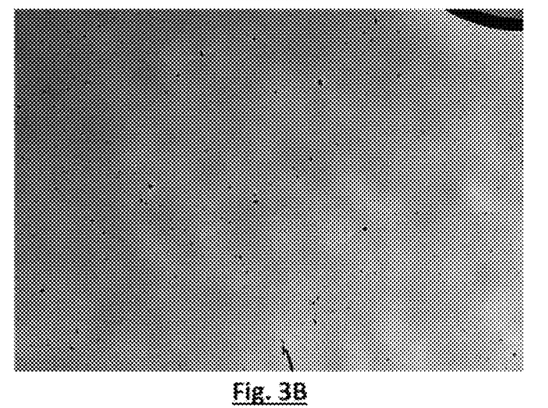
FIGS. 3B and 3C show images of a sample including between 300 and 350 copies of a target sequence, the images being acquired 38 minutes and 40 minutes after the target sequences and a reaction medium containing amplification reagents were mixed, respectively.

FIG. 3B is an image acquired by the image sensor 16 thirty-eight minutes after the mixing of a second sample with the reaction medium. The second sample contained 1000 copies of the target sequence in a volume of 25 μl. The observed volume was estimated to be 8 μl, this corresponding to about 300 to 350 copies. The image is relatively uniform. The formation of pyrophosphate precipitates is still not observable in the image.

Figure 3C:
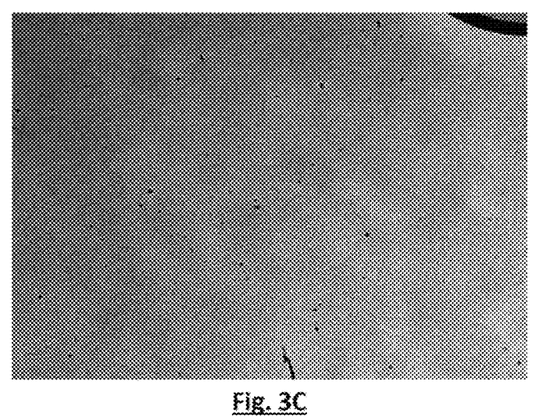

FIG. 3C is an image acquired by the image sensor 40 minutes after the mixing of the second sample with the reaction medium. The texture of the image is clearer than in the image 3B acquired only 2 minutes earlier.

The inventors have observed that the use of moments, and in particular the variance or standard deviation, allows the variation in the turbidity of the image, resulting from the formation of magnesium-pyrophosphate precipitates under the effect of the amplification process, to be quantified. With each image may be associated an indicator, called the amplification indicator, calculated from such moments. Trials were carried out with various samples, respectively containing an initial amount of target sequence evaluated to be 21 copies (samples A1 and A2), 210 copies (samples B1 and B2), 2100 copies (samples C1 and C2), 21000 copies (samples D1 and D2) and 210000 copies (samples E1 and E2). Trials were also carried out on two samples called negative control samples, containing the reaction medium but no target nucleotide sequence (samples N1 and N2). The images were acquired at an acquisition frequency of 1 image per minute. In each acquired image, a region of interest was selected visually, and the standard deviation of a gray-scale distribution of the pixels was determined in the region of interest. When the initial amount of target sequences exceeded 20000 copies, the region of interest was the entire acquired image.

Figure 3D:
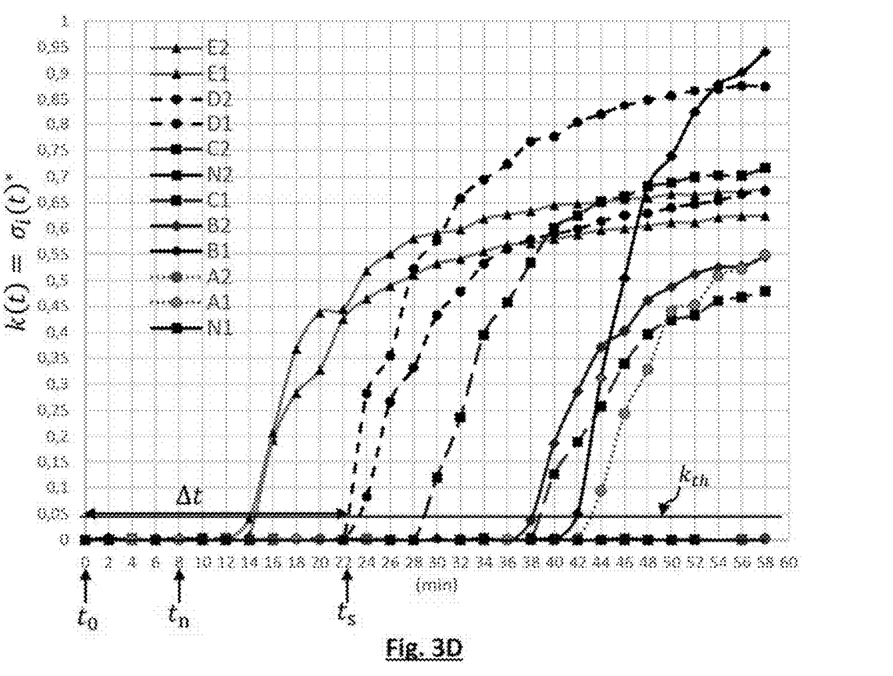
FIG. 3D illustrates a temporal variation in an amplification indicator, obtained from images of various samples.

FIG. 3D shows the temporal variation in a normalized standard deviation between the various acquired images, for each analyzed sample. The x-axis of this figure represents time passed from the initial time $t_0$, expressed in minutes. The y-axis represents a value of what is called a normalized standard deviation $\sigma_i(t)^*$, obtained from the images acquired by the image sensor observing a sample i, this standard deviation being defined by the following expression:

$$k(t) = \sigma_i(t)^* = \frac{\sigma_i(t) - \overline{\sigma_i(t_0, t_n)}}{\sigma_{Max} - \sigma_{min}}$$

where:

$\sigma_i(t)$ is the standard deviation of an image acquired at a time t for a sample i;

$\overline{\sigma_i(t_0,t_n)}$ is the average standard deviation of images acquired between the initial time $t_0$ and a time $t_n$ called a nearby time, the nearby time being sufficiently close to the initial time that the acquired image does not change significantly between the initial time $t_0$ and the nearby time $t_n$ under the effect of the amplification. In this example, the nearby time $t_n$ is equal to 8 minutes after the initial time. This average standard deviation allows fluctuations in the acquired image due to the effect of the noise of the image sensor 16 or fluctuations in the light source 11 to be accounted for.

$\sigma_{Max}$ is the maximum standard deviation measured in all the images of the set of samples in question.

$\sigma_{min}$ is the minimum standard deviation measured in all the images of the set of samples in question.

i designates the sample.

For each amount in question of target sequences, two different samples were examined. It was observed that it was possible to detect an amplification when the initial amount of target sequences was small, for example 20 copies in 8 μl. The length of time Δt required before amplification is detected theoretically depends on the initial amount of target sequences. In FIG. 3D, this length of time may be determined by identifying the threshold time $t_s$ at which the amplification indicator k(t) in question, in the present case the normalized standard deviation, exceeds a preset threshold value $k_{th}$. The initial time $t_0$ corresponds to the mixing of the sample and the reaction medium. In this example, the threshold value $k_{th}$ is set to 0.05. It was observed that when the initial amount of target sequences was small, typically smaller than $2.1 \times 10^3$ copies, the time $t_s$ at which the threshold is crossed could not be accurately related to an initial quantity. Thus, for small initial quantities of target sequences, the implemented method is qualitative: it allows amplification of a target value to be observed, without however allowing the initial amount of target sequence to be accurately quantified.

When the initial amount is increased, for example to $2.1 \times 10^4$, $2.1 \times 10^5$ or $2.1 \times 10^6$ copies, the detection is quantitative, the time $t_s$ at which the threshold is crossed being correlated to the amount of target sequence initially present in the sample. An example of the length of time Δt taken to cross the threshold and the crossover time $t_s$ is shown in FIG. 3D, with regard to the sample D1.

These trials show that the standard deviation of each acquired image forms an exploitable amplification indicator.

Figure 3E:
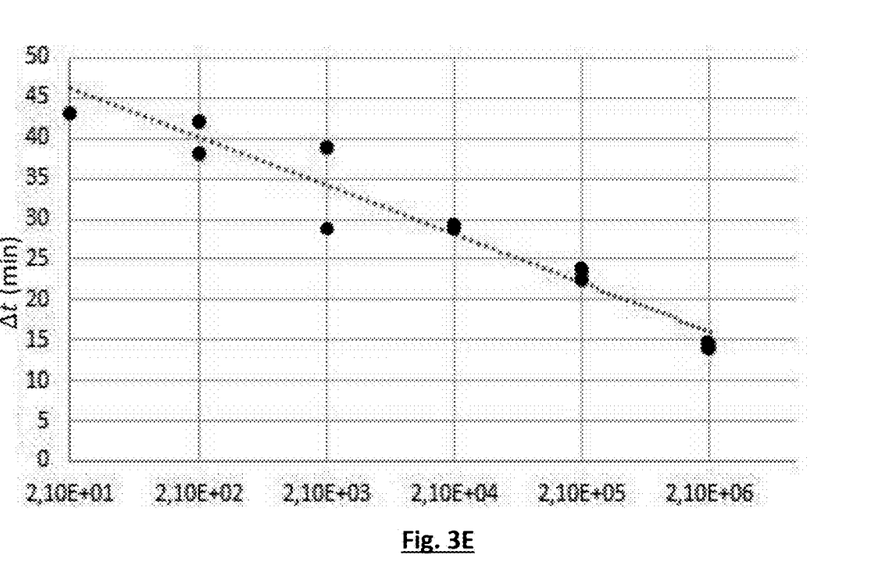
FIG. 3E shows a relationship between the initial concentration of target sequence in the sample and the time taken, after the target sequences were mixed with the amplification reagents, to obtain an amplification indicator exceeding a preset threshold.

FIG. 3E shows the variation in the length of time Δt taken to cross the threshold as a function of the initial amount of target sequences in the sample.

Figure 4A:
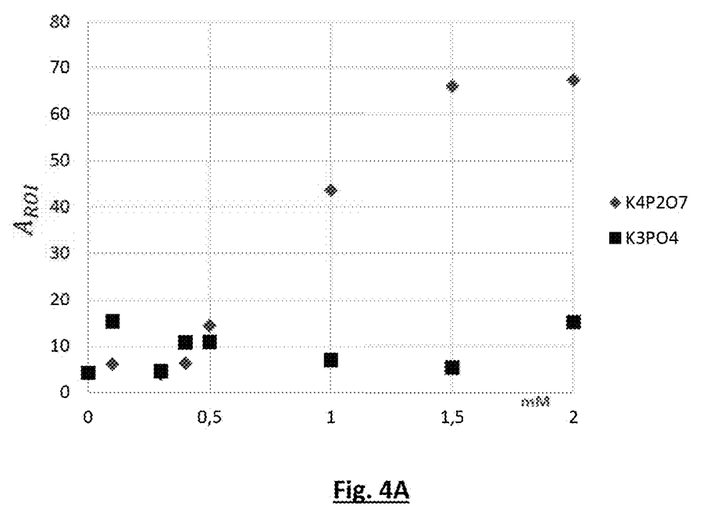
FIG. 4A shows a variation in a statistical indicator obtained from images of samples containing manganese chloride and various concentrations of potassium pyrophosphate or potassium phosphate—this statistical indicator being representative of an amplification indicator.

In another series of trials, the inventors have verified that a variation in the turbidity of a sample may be observed under the effect of the formation of compounds other than magnesium pyrophosphate. Thus, the device described above was employed to detect the formation of manganese pyrophosphate $MnP_2O_7$. Various samples including an aqueous solution of manganese chloride $Cl_2Mn$, of 4 mM concentration, were observed with the device. The samples contained either potassium phosphate ($K_3PO_4$), or potassium pyrophosphate ($K_4P_2O_7$), the concentration of $K_3PO_4$ or of $K_4P_2O_7$ varying between 0 and 2 mM. A manganese-containing precipitate forms only in the presence of potassium pyrophosphate, potassium phosphate being a monophosphate. One image was acquired for each sample. In each acquired image, one or more regions of interest corresponding to a structured portion of the image were delineated, analogously to FIG. 3A. Next, the area $A_{ROI}$ of the selected regions of interest relative to the total area of the image was determined. FIG. 4A shows the results obtained: the x-axis corresponds to the concentration of $K_3PO_4$ or of $K_4P_2O_7$, the y-axis representing the relative area $A_{ROI}$ of the regions of interest, which was defined beforehand. It may clearly be seen that, in the presence of potassium pyrophosphate, a precipitate of manganese pyrophosphate ($MnP_2O_7$) formed when the concentration of $K_4P_2O_7$ exceeded 0.5 mM.

Figure 4B:
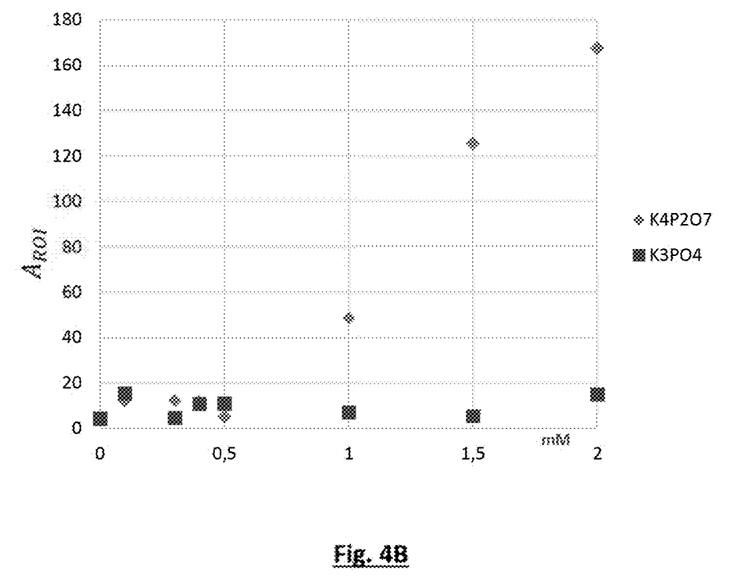
FIG. 4B shows a variation in the indicator described with reference to FIG. 4A, based on images of samples including magnesium sulfate and various concentrations of potassium pyrophosphate or potassium phosphate.

The same experiment was carried out again, using samples containing a concentration of 4 mM of magnesium sulfate ($MgSO_4$). The samples either contained potassium phosphate ($K_3PO_4$) or potassium pyrophosphate ($K_4P_2O_7$), the concentration in $K_3PO_4$ or in $K_4P_2O_7$ varying between 0 and 2 mM. Just as in the preceding experiment, a magnesium-containing precipitate formed only in the presence of potassium pyrophosphate. Similarly to what was described with reference to FIG. 4A, one image was acquired for each sample. In each acquired image, one or more regions of interest, corresponding to structured portions of the image, were delineated. The area $A_{ROI}$ of the regions of interest relative to the area of the image was then determined. FIG. 4B shows the obtained results: the x-axis corresponds to the concentration in $K_3PO_4$ or in $K_4P_2O_7$, the y-axis representing the relative area of the regions of interest $A_{ROI}$. It may dearly be seen that, in the presence of potassium pyrophosphate, a precipitate of magnesium pyrophosphate formed when the concentration in $K_4P_2O_7$ exceeded 0.5 mM.

This shows that the device allows small amounts of pyrophosphate precipitates (i.e. amounts larger than or equal to 0.5 mM or 1 mM) to be observed, whether the precipitate is magnesium pyrophosphate or manganese pyrophosphate.

Figure 4C:
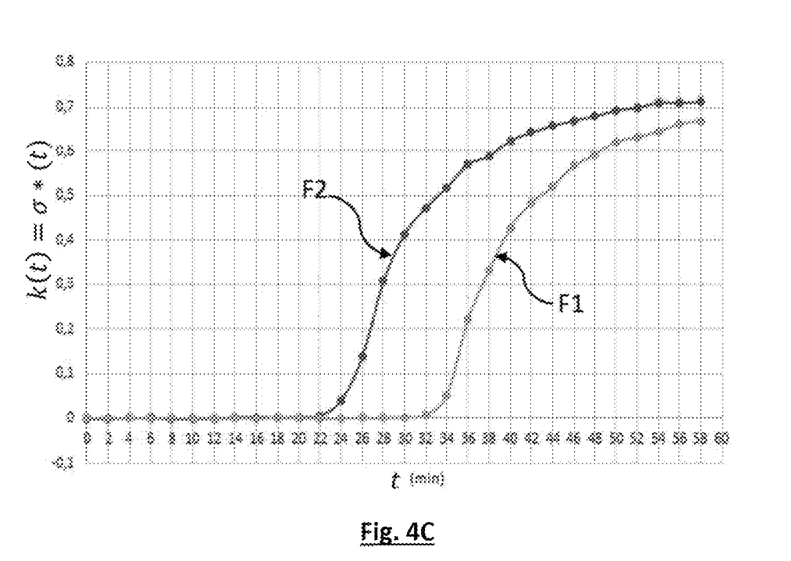
FIG. 4C shows the variation in an amplification indicator of two samples containing the same initial amount of target sequence, one of the two samples containing an initial amount of potassium pyrophosphate obtained by adding potassium pyrophosphate.

According to one embodiment, the reaction medium includes an initial amount of pyrophosphate ions, for example in a concentration preferably lower than 0.5 mM, 0.4 mM for example. These ions may result from the introduction, into the sample, of a pyrophosphate salt, $K_4P_2O_7$ for example. This allows the amount of pyrophosphate ions resulting from the amplification and allowing said amplification to be detected optically, for example using the amplification indicator described above, to be decreased. The crossing of the threshold $k_{th}$ (which was mentioned with reference to FIG. 3D) is reached more rapidly. This makes it possible to lower the detection limit of the method, i.e. to decrease the initial amount of target sequences the amplification of which is observable, in a given length of time, in an image of the sample. This also allows the amplification process to be observed more rapidly. FIG. 4C shows a temporal variation in the standard deviation of images acquired of two samples F1 and F2 containing an initial amount of 22 copies per microliter. $K_4P_2O_7$ in an amount of 0.4 mM was added to the sample F2 beforehand. Just as in the trials presented in FIG. 3D, images of each sample were acquired at an acquisition frequency of 1 image per minute, and the normalized standard deviation of the images was determined as described above. FIG. 4C shows the temporal variation in the normalized standard deviation, the latter playing the role of dispersion indicator. It may be seen that with the sample F2, containing the initial amount of potassium pyrophosphate, the dispersion indicator increases more rapidly than in the sample F1. Thus, the prior addition of potassium pyrophosphate allows the rapidity of detection of the method and the detection limit to be improved. It will be noted that such an effect is not only of relevance to a LAMP amplification method; on the contrary, it is generalizable to any amplification method provided that it is accompanied by the formation of precipitates. This is in particular the case of the aforementioned PCR method.

Figure 5A:
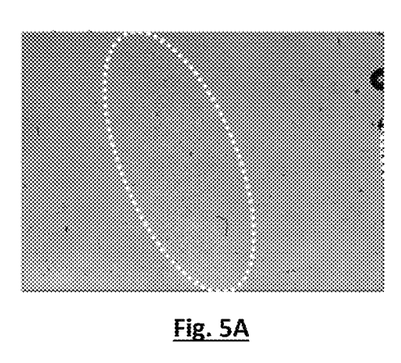
FIGS. 5A and 5B show images of samples containing the same initial amount of target sequences; the images were obtained while the samples were illuminated with a spatially coherent light source, the images being acquired 38 minutes after the target sequences and a reaction medium containing amplification reagents were mixed.
Figure 5B:
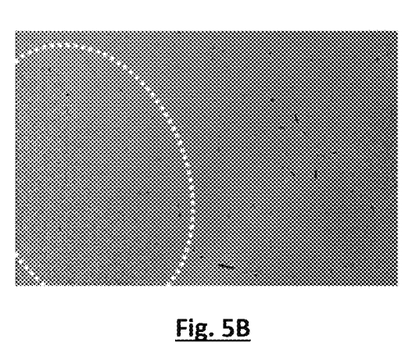
Figure 5C:
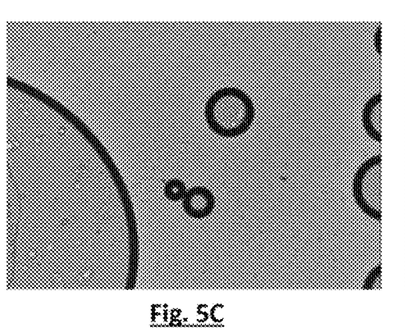
FIGS. 5C and 5D show images of samples containing the same initial amount of target sequences; the images were obtained while the samples were illuminated with a non-spatially coherent light source, the images being acquired 38 minutes after the target sequences and the reaction medium were mixed.
Figure 5D:
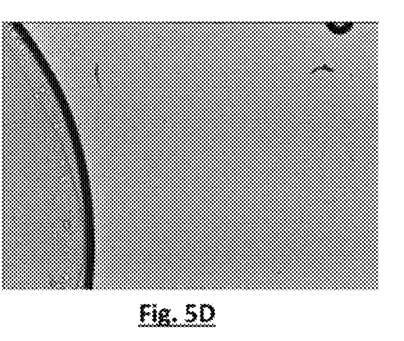

In another series of trials, images were respectively acquired with and without a spatial filter 18 placed between the light source 11 and the fluidic chamber 15. FIGS. 5A and 5B respectively show images acquired using two samples G1 and G2 such as described above, containing an initial amount of 100 copies of the target sequence. These images were obtained 38 minutes after the mixing of the reaction medium and the target sequences. The device includes a spatial filter taking the form of a pinhole diaphragm 18 such as described with reference to FIG. 1. FIGS. 5C and 5D show images acquired using two samples G3 and G4 that were identical to the samples G1 and G2, 38 minutes after having been mixed with the reaction medium and without a spatial filter 18 placed between the light source 11 and the fluidic chamber 15. In such a configuration the light source is not spatially coherent. The image obtained simply reflects the effect of attenuation of the light by the sample mixed with the reaction medium. As may be seen by comparing, on the one hand, FIGS. 5A and 5B, and on the other hand, FIGS. 5C and 5D, when the light source 11 is not spatially coherent, i.e. in the configuration associated with FIGS. 5C and 5D, the image provides no exploitable information. In contrast, in the images 5A and 5B, the image may clearly be seen to contain structuring, in the encircled zones of interest, because of the formation of diffraction patterns by the precipitates 10p resulting from the amplification process. In FIGS. 5C and 5D, the zones encircled by dark lines correspond to air bubbles.

Figure 5E:
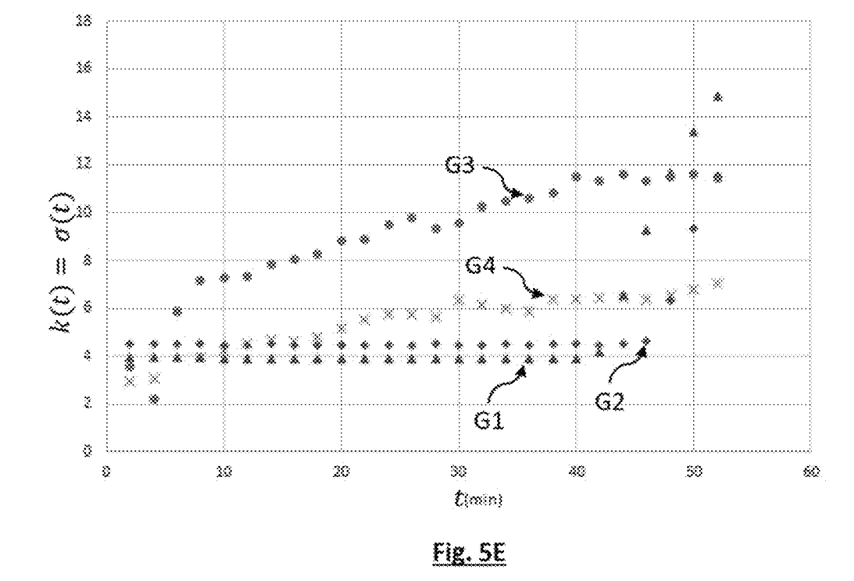
FIG. 5E illustrates a temporal variation in an amplification indicator obtained from images of a sample, with and without a spatial filter interposed between the light source and the sample, respectively.

A series of images was acquired of each of the samples G1, G2, G3 and G4: two series of images were acquired with a spatial filter 18 (samples G1 and G2) between the fluidic chamber 15 and the light source 11, and two series of images were acquired without a spatial filter (samples G3 and G4). In each image, a standard deviation, playing the role of amplification indicator, was calculated. FIG. 5E shows the temporal variation in the amplification indicator k(t) corresponding to the standard deviation of each acquired image. It may be seen that by implementing the spatial filter (samples G1 and G2), the threshold time, at which the amplification indicator exceeds a threshold value, is clearly identifiable: the temporal variation has a flat portion, up to t=45 minutes, then sees an abrupt increase. Without spatial filter (samples G3 and G4), the variation in the amplification indicator is less clear, and does not exhibit the inflection observed by implementing the spatial filter.

These trials show that the method is essentially based on spatialized detection of diffraction patterns formed by the precipitates 10p, unlike prior-art methods based on attenuation of an incident light beam. The method according to the invention allows precipitates resulting from the amplification of the target sequence to be detected earlier.

According to one embodiment, the indicator for tracking the amplification is established from an image of interest resulting from application of a numerical propagation operator to the acquired image $I_0$. Specifically, the acquired image may not sufficiently represent the sample and a more exploitable representation may be obtained, from the acquired image, by applying a propagation operator so as to calculate a quantity representative of the exposure light wave 14 to which the image sensor 16 is exposed. Such a method, which is referred to as holographic reconstruction, in particular allows an image of the modulus or phase of this light wave 14 to be reconstructed in a reconstruction plane parallel to the detection plane $P_0$, and in particular in the plane $P_{10}$ in which the sample lies. To do this, the image $I_0$ acquired by the image sensor 16 is convoluted with the propagation operator h in order to obtain a convolution product. It is then possible to calculate a complex expression A for the light wave 14 at any point of spatial coordinates (x, y, z), and in particular on a reconstruction surface lying facing the image sensor. The reconstruction surface may in particular be a reconstruction plane $P_z$ located at a distance |z| from the image sensor 16, this reconstruction plane preferably being a plane $P_{10}$ in which the sample lies; then: $A(x,y,z)=I_0(x,y,z)*h$, where * represents the convolution operator.

In the rest of this description, the coordinates (x,y) indicate a radial position in a plane perpendicular to the propagation axis Z. The coordinate z being a coordinate along the propagation axis Z.

The complex expression A is a complex quantity the argument and modulus of which are respectively representative of the phase and intensity of the light wave 14 to which the image sensor 16 is exposed. Convoluting the image $I_0$ with the propagation operator h allows a complex image $A_z$ representing a spatial distribution of the complex expression A, in the reconstruction plane $P_z$ located at a coordinate z from the detection plane $P_0$, to be obtained. In this example, the equation of the detection plane $P_0$ is z=0. The complex image $A_z$ corresponds to a complex image of the sample in the reconstruction plane $P_z$. It also represents a two-dimensional spatial distribution of the optical properties of the exposure light wave 14. The function of the propagation operator h is to describe the propagation of the light between the image sensor 16 and a point of coordinates (x, y, z) located at a distance |z| from the image sensor. It is then possible to determine the modulus $M(x,y,z)$ and/or phase $\phi(x,y,z)$ of the exposure light wave 14 at this distance |z|, called the reconstruction distance, using:

$M(x,y,z)=abs[A(x,y,z)]$; and $\phi(x,y,z)=arg[A(x,y,z)]$;

the operators abs and arg respectively returning the modulus and argument.

In other words, the complex expression A of the exposure light wave 14 at any point of spatial coordinates (x, y, z) is such that: $A(x,y,z)=M(x,y,z)e^{j\phi(x,y,z)}$. It is possible to form images $M_z$ and $\phi_z$ that respectively represent a distribution of the modulus or phase of the complex expression A on a surface lying facing the detection plane $P_0$. Such a surface may in particular be a plane $P_z$ located at a distance |z| from the detection plane $P_0$, with $M_z=mod(A_z)$ and $\phi_z=arg(A_z)$. The aforementioned surface is not necessarily planar, though it preferably lies parallel to the detection plane and is preferably a plane $P_z$ parallel to the detection plane. In the rest of the description, the image obtained from the modulus and/or phase of the complex image $A_z$ is referred to as the "reconstructed image" and is denoted $I_z$.

Figure 2B:
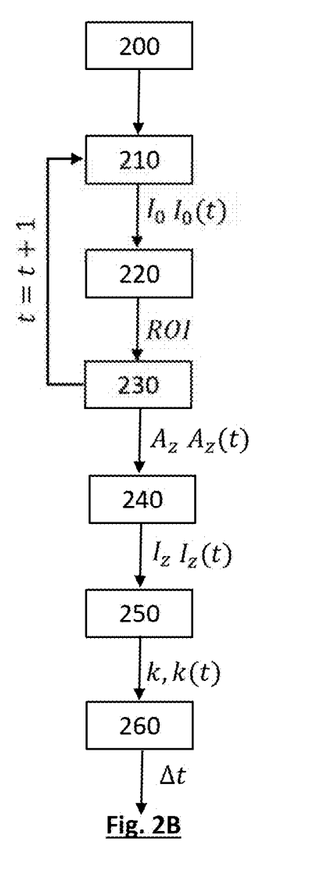
FIG. 2B shows the mains steps of another embodiment.

The main steps of this embodiment are shown in FIG. 2B. Steps 200, 210 and 220 are respectively identical to the steps 100, 110 and 120 described above. The step 220 of selecting a region of interest is optional, steps 230 to 250 being equally applicable to the entire image acquired by the image sensor as to a selected region of interest.

Step 230: calculation of a complex image $A_z$ on a reconstruction surface, ideally a reconstruction plane $P_z$, lying facing the image sensor. The complex image contains information on the phase and amplitude of the exposure light wave 14 to which the image sensor 16 is exposed. The reconstruction plane is a plane that is advantageously perpendicular to the propagation axis Z, and/or parallel to the detection plane $P_0$. It is preferably a plane $P_{10}$ in which the sample lies. Step 230 may be carried out by applying the propagation operator h described above to an image obtained from the acquired image $I_0$, or to the selected region of interest ROI. However, application of the propagation operator to the acquired image may result in a complex image $A_z$ that is affected by substantial reconstruction noise, this noise commonly being referred to as "twin images". In order to obtain an exploitable complex image, while limiting reconstruction noise, iterative algorithms may be employed. An example algorithm is described in French patent application FR1652500, filed 23 Mar. 2016. The complex image $A_z$ represents the various values of the complex amplitude $A(x,y,z)$ in the reconstruction plane $P_z$.

Step 240: formation of an image of interest, representative of the sample. From the complex image $A_z$ it is possible to obtain a reconstructed image $I_z$ of the modulus $M_z$ and/or phase $\phi_z$ of the exposure light wave 14, in the reconstruction plane $P_z$. The reconstruction distance with respect to the image sensor is determined either a priori, the position of the sample 10 with respect to the image sensor 16 being known, or using a digital focusing algorithm, the optimal reconstruction distance then being that at which the reconstructed image $I_z$ is clearest. Digital focusing algorithms are known to those skilled in the art. The reconstructed image $I_z$ forms the image of interest.

Step 250: application of a statistical indicator to the image of interest $I_z$. This indicator may be a mean, a median or a moment such as described above. It may in particular be the variance. Application of the statistical indicator k allows the amplification indicator to be obtained.

Steps 200 to 230 may be repeated, so as to obtain, in succession, various images acquired by the image sensor. As many complex images $A_z(t)$ are then obtained, from which as many reconstructed images $I_z(t)$ and amplification-tracking indicators are determined. This allows a temporal variation k(t) of the amplification indicator to be obtained. Just as in step 240 described above, it is possible to determine a threshold time $t_s$ at which the tracking indicator crosses a threshold $k_{th}$, so as to estimate a length of time $\Delta t$ between the threshold time $t_s$ and the initial time $t_0$, the latter corresponding to the mixing of the sample and the reaction medium.

Although described with reference to a LAMP amplification method, the invention may be used to track any amplification method provided that the latter is accompanied by the formation of precipitates in a concentration higher than 0.5 mM or 1 mM. Thus, the invention may for example be applied to PCR or RBA (recombinase polymerase amplification) methods.

The invention claimed is:

1. A method for tracking the in-vitro amplification of a nucleotide sequence contained in a sample, the amplification aiming to replicate said nucleotide sequence via a DNA polymerase enzyme, the method comprises the following steps:

a) mixing the sample with a reaction medium so as to obtain multiple replications of a preset nucleotide target sequence, the mixing being carried out at an initial time;

b) illuminating the sample using a point light source, the point light source emitting, in an illumination spectral band, an incident light wave that propagates toward the sample;

c) acquiring, using an image sensor, a two-dimensional image of the sample, the sample being placed between the point light source and the image sensor such that the image sensor is exposed to an exposure light wave having passed through the sample, the acquisition being carried out at an acquisition time subsequent to the initial time;

d) on the basis of the acquired image, forming an image of interest that is representative of the formation of a precipitate in the sample under the effect of the amplification; and e) calculating an indicator, called the amplification indicator, depending on a distribution of the intensity of the pixels in all or part of the image of interest, the amplification indicator being representative of a replicated amount of target sequences;

wherein, in step c), the image is acquired in the illumination spectral band, and wherein the amplification indicator is determined depending on a dispersion of the intensity of the pixels in the image of interest.

2. The method of claim 1, wherein, in step d), the image of interest is formed by the acquired image or by a region of interest of the acquired image.

3. The method of claim 1, wherein step d) comprises the following substeps:
- to all or part of the image acquired in step c), applying a propagation operator so as to calculate a complex amplitude of the exposure light wave, on a reconstruction surface lying facing the image sensor; and
- on the basis of the complex amplitude, forming an image, called the reconstructed image, representative of the modulus and/or phase of the complex amplitude on the reconstruction surface, the reconstructed image forming the image of interest.

4. The method of claim 1, wherein, in step e), the amplification indicator is obtained from a moment of order strictly higher than 1 of the distribution of the pixel intensity of the image of interest.

5. The method of claim 1, wherein the amplification indicator is obtained from a variance or a standard deviation of the distribution of the pixel intensity of the image of interest.

6. The method of claim 1, wherein steps a) to e) are carried out at various acquisition times, the method then comprising, a step f), temporally tracking the value of the amplification indicator at said acquisition times.

7. The method of claim 1, comprising a step g) of detecting a time, called the threshold time, at which the amplification indicator passes a threshold value, so as to obtain a time span between the threshold time and the initial time.

8. The method of claim 1, wherein the amplification is achieved by polymerase-chain-reaction amplification.

9. The method of claim 1, wherein the sample is contained in a fluidic chamber the thickness of which is smaller than 1 mm, the area of the sample observed by the image sensor being larger than 10 $mm^2$.

10. The method of claim 1, wherein the exposure light wave includes an incident light-wave portion having passed through the sample and a diffracted wave resulting from diffraction by the sample of the incident light wave, the diffraction resulting from the precipitate within the sample.

11. The method of claim 1, wherein no magnifying optics are placed between the image sensor and the sample.

12. The method of claim 1, wherein there is no fluorescent or colored dye provided in the sample.

13. The method of claim 1, wherein the amplification is achieved by loop-mediated isothermal amplification reaction.

* * * * *